United States Patent [19]

Powell et al.

[11] Patent Number: 5,770,776
[45] Date of Patent: Jun. 23, 1998

[54] PROCESS FOR PREPARING 1,3-PROPANEDIOL

[75] Inventors: Joseph Broun Powell, Houston; Stephen Blake Mullin, Katy; Paul Richard Weider; David Cleve Eubanks, both of Houston; Juan Pedro Arhancet, Katy, all of Tex.

[73] Assignee: Shell Oil Company, Houston, Tex.

[21] Appl. No.: 615,544

[22] Filed: Mar. 11, 1996

Related U.S. Application Data

[63] Continuation-in-part of Ser. No. 316,676, Sep. 30, 1994, abandoned.

[51] Int. Cl.$^6$ .................................................. C07C 29/36
[52] U.S. Cl. ............................ 568/862; 568/483; 568/852
[58] Field of Search ...................................... 568/852, 862

[56] References Cited

U.S. PATENT DOCUMENTS

| | | | |
|---|---|---|---|
| 3,168,553 | 2/1965 | Slaugh | 260/497 |
| 3,456,017 | 7/1969 | Smith | 260/602 |
| 3,463,819 | 8/1969 | Smith | 260/602 |
| 3,687,981 | 8/1972 | Lawrence | 260/340.7 |
| 4,137,240 | 1/1979 | Peterson | 260/340.7 |
| 4,255,279 | 3/1981 | Spohn | 252/413 |
| 4,404,119 | 9/1983 | Lagace | 252/413 |
| 4,873,378 | 10/1989 | Murphy | 568/867 |
| 5,030,766 | 7/1991 | Briggs et al. | 568/852 |
| 5,210,318 | 5/1993 | Briggs | 568/496 |
| 5,256,827 | 10/1993 | Slaugh | 568/454 |
| 5,463,145 | 10/1995 | Powell | 568/867 |

*Primary Examiner*—Rebecca Cook

[57] ABSTRACT

1,3-propanediol is prepared in a process in which ethylene oxide is reacted with carbon monoxide and hydrogen in an essentially non-water-miscible solvent in the presence of an effective amount of a non-phosphine-ligated cobalt catalyst and an effective amount of a catalyst promoter under reaction conditions effective to produce an intermediate product mixture comprising less than about 15 wt % 3-hydroxypropanal. The 3-hydroxypropanal is extracted in water from the product mixture in more concentrated form, with the majority of the cobalt catalyst remaining in the solvent phase for recycle to the hydroformylation reaction. At least a portion of any residual catalyst in the water phase following extraction is removed by re-extraction with non-water-miscible solvent and recycled to hydroformylation. The 3-hydroxypropanal is then hydrogenated in aqueous solution to the desired 1,3-propanediol.

17 Claims, 1 Drawing Sheet

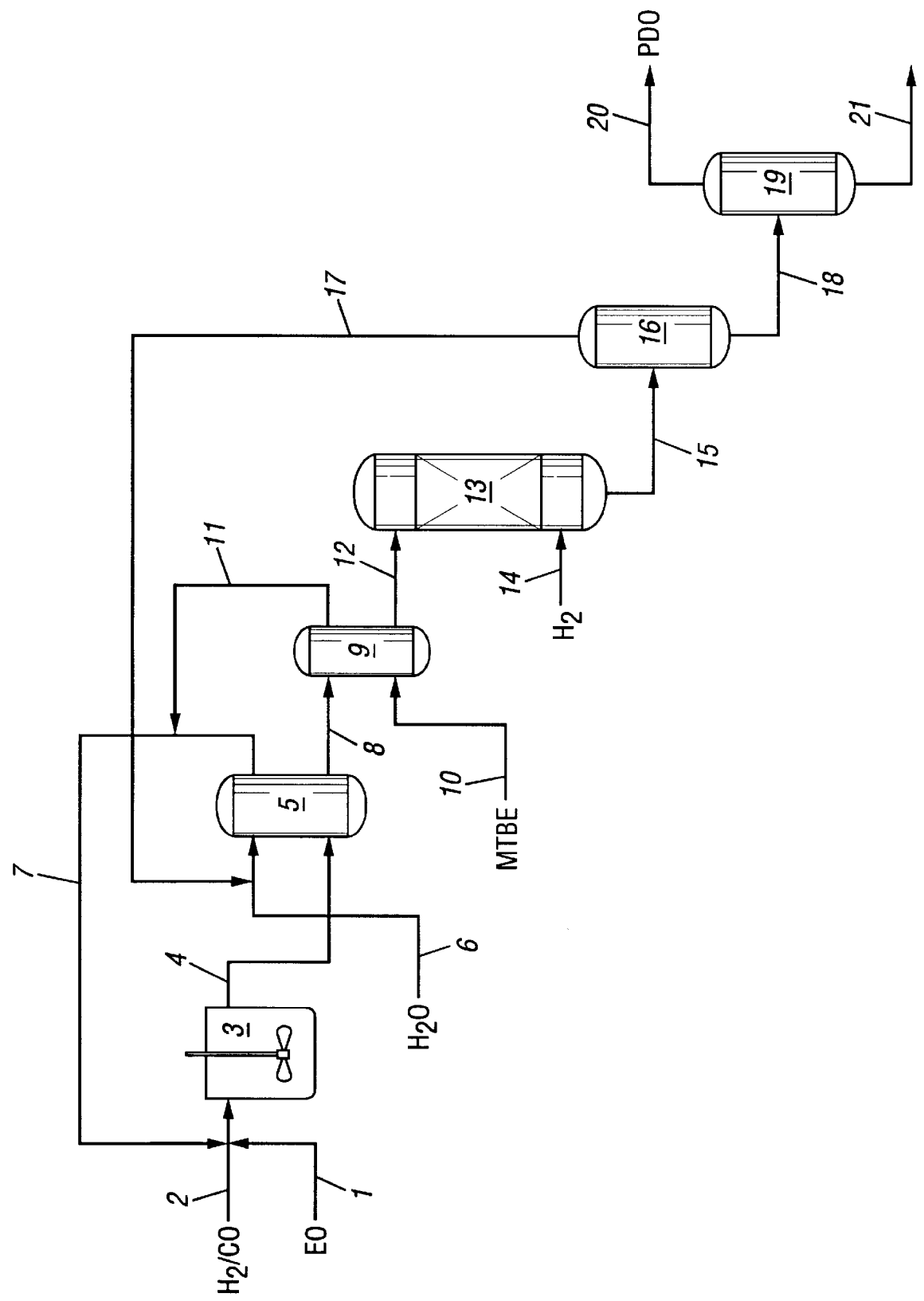

PROCESS FOR PREPARING 1,3-PROPANEDIOL

CROSS-REFERENCE TO RELATED APPLICATION

This application is a continuation-in-part of Ser. No. 316,676, filed Sep. 30, 1994 abandoned.

BACKGROUND OF THE INVENTION

This invention relates to the preparation of 1,3-propanediol. In one aspect, the invention relates to a cobalt-catalyzed process for manufacturing 1,3-propanediol in high yields without the use of a phosphine ligand for the cobalt catalyst. In a specific aspect, the invention relates to improving the degree of recovery and recycle of the cobalt catalyst in such a process.

1,3-propanediol (PDO) is an intermediate in the production of polyesters for fibers and films. It is known to prepare PDO in a two-step process involving (1) the cobalt-catalyzed hydroformylation (reaction with synthesis gas, $H_2/CO$) of ethylene oxide to intermediate 3-hydroxypropanal (HPA) and (2) hydrogenation of the HPA to PDO. The initial Hydroformylation step can be carried out at temperatures greater than 100° C. and at high syngas pressures to achieve practical reaction rates. The resulting product mixture is, however, rather unselective for HPA.

In an alternate hydroformylation method, the cobalt catalyst is used in combination with a phosphine ligand to prepare HPA with greater selectivity and at lower temperature and pressure. However, the use of a phosphine ligand adds to the cost of the catalyst and increases the complexity of catalyst recycle.

It would be desirable to prepare HPA in a low temperature, selective process in which cobalt catalyst recovery was inexpensive but essentially complete.

It is therefore an object of the invention to provide, in a process for the preparation of 1,3-propanediol which does not require the use of a phosphine-ligated catalyst for preparation of the HPA intermediate, essentially complete recovery and recycle of the cobalt catalyst.

SUMMARY OF THE INVENTION

According to the invention, 1,3-propanediol is prepared in a process comprising the steps of:

(a) contacting ethylene oxide with carbon monoxide and hydrogen in an essentially non-water-miscible solvent in the presence of an effective amount of a non-phosphine-ligated cobalt catalyst and an effective amount of a catalyst promoter, under reaction conditions effective to produce an intermediate product mixture comprising less than about 15 wt % 3-hydroxypropanal;

(b) adding an aqueous liquid to said intermediate product mixture and extracting into said aqueous liquid a major portion of the 3-hydroxypropanal to provide an aqueous phase comprising 3-hydroxypropanal in greater concentration than the concentration of 3-hydroxypropanal in said intermediate product mixture, and an organic phase comprising a major portion of the cobalt catalyst or a cobalt-containing derivative thereof;

(c) separating the aqueous phase from the organic phase;

(d) adding fresh non-water miscible solvent to said aqueous phase and extracting into said fresh solvent at least a portion of any cobalt catalyst or cobalt-containing derivative thereof present in such aqueous phase, to provide a second aqueous phase comprising 3-hydroxypropanal and a second organic phase comprising the cobalt catalyst or a cobalt-containing derivative thereof;

(e) separating the second aqueous phase from the second organic phase;

(f) passing the first organic phase and the second organic phase to the reaction of step (a);

(g) contacting the second aqueous phase comprising 3-hydroxypropanal with hydrogen in the presence of a hydrogenation catalyst under hydrogenation conditions to provide a hydrogenation product mixture comprising 1,3-propanediol; and (h) recovering 1,3-propanediol from said hydrogenation product mixture.

The process enables the production of 1,3-propanediol in high yields and selectivity without the use of a phosphine-ligated cobalt catalyst in the hydroformylation step, with enhanced recovery and recycle of the cobalt catalyst.

BRIEF DESCRIPTION OF THE DRAWING

FIG. 1 is a schematic flow diagram of one embodiment of the invention 1,3-propanediol preparation process with enhanced cobalt recovery.

DETAIL DESCRIPTION OF THE INVENTION

The invention 1,3-propanediol preparation process can be conveniently described by reference to FIG. 1. Separate or combined streams of ethylene oxide 1, carbon monoxide and hydrogen 2 are charged to hydroformylation vessel 3, which can be a pressure reaction vessel such as a bubble column or agitated tank, operated batchwise or in a continuous manner. The feed streams are contacted in the presence of a non-phosphine-ligated cobalt catalyst, i.e., a cobalt carbonyl composition which has not been prereacted with a phosphine ligand. The hydrogen and carbon monoxide will generally be introduced into the reaction vessel in a molar ratio within the range of about 1:2 to about 8:1, preferably about 1.5:1 to about 5:1.

The reaction is carried out under conditions effective to produce a hydroformylation reaction product mixture containing a major portion of 3-hydroxypropanal (HPA) and a minor portion of acetaldehyde and 1,3-propanediol, while maintaining the level of 3-hydroxypropanal in the reaction mixture at less than 15 wt %, preferably within the range of about 5 to about 10 wt %. (To provide for solvents having different densities, the desired concentration of HPA in the reaction mixture can be expressed in molarity, i.e., less than 1.5M, preferably within the range of about 0.5 to about 1M.) The hydroformylation reaction is carried out at elevated temperature generally less than 100° C., preferably about 60° to about 90° C., most preferably about 75° to about 85° C., and at a pressure within the range of about 500 to about 5000 psig, preferably (for process economics) about 1000 to about 3500 psig, with higher pressures preferred for greater selectivity. The concentration of 3-hydroxypropanal in the intermediate product mixture can be controlled by regulation of process conditions such as ethylene oxide concentration, catalyst concentration, reaction temperature and residence time. In general, relatively low reaction temperatures (below about 90° C.) and relatively short residence times (about 20 minutes to about 1 hour) are preferred. In the practice of the invention method, it is possible to achieve HPA yields (based on ethylene oxide conversion) of greater than 80%, with formation of greater than 7 wt % HPA, at rates greater than 30 h$^{-1}$. (Catalytic rates are referred to herein in terms of "turnover frequency" or "TOF" and are expressed in units of moles per mole of cobalt per hour, or h$^{-1}$.) Reported rates are based on the observation that, before a majority of EO is converted, the reaction is essentially zero-order in ethylene oxide concentration and proportional to cobalt concentration.

The hydroformylation reaction is carried out in a liquid solvent inert to the reactants. By "inert" is meant that the solvent is not consumed during the course of the reaction. In general, ideal solvents for the phosphine ligand-free process will solubilize carbon monoxide, will be essentially non-water-miscible and will exhibit low to moderate polarity such that the 3-hydroxypropanal intermediate will be solubilized to the desired concentration of at least about 5 wt % under hydroformylation conditions, while significant solvent will remain as a separate phase upon water extraction. By "essentially non-water-miscible" is meant that the solvent has a solubility in water at 25° C. of less than 25 wt %, so as to form a separate hydrocarbon-rich phase upon water extraction of HPA from the hydroformylation reaction mixture. Preferably this solubility is less than about 10%, most preferably less than about 5 wt %. The solubilization of carbon monoxide in the selected solvent will generally be greater than 0.15 v/v (1 atm, 25° C.), preferably greater than 0.25 v/v, as expressed in terms of Ostwald coefficients.

The preferred class of solvents are alcohols and ethers which can be described according to the formula

$$R_2\text{—}O\text{—}R_1 \quad (1)$$

in which $R_1$ is hydrogen or $C_{1-20}$ linear, branched, cyclic or aromatic hydrocarbyl or mono- or polyalkylene oxide and $R_2$ is $C_{1-20}$ linear, branched, cyclic or aromatic hydrocarbyl, alkoxy or mono- or polyalkylene oxide. The most preferred hydroformylation solvents can be described by the formula

$$\begin{array}{c} R_3 \\ | \\ R_4\text{—}C\text{—}O\text{—}R_1 \\ | \\ R_5 \end{array} \quad (2)$$

in which $R_1$ is hydrogen or $C_{1-8}$ hydrocarbyl, and $R_3$, $R_4$ and $R_5$ are independently selected from $C_{1-8}$ hydrocarbyl, alkoxy and alkylene oxide. Such ethers include, for example, methyl-t-butyl ether, ethyl-t-butyl ether, diethyl ether, phenylisobutyl ether, ethoxyethyl ether, diphenyl ether and diisopropyl ether. Blends of solvents such as tetrahydrofuran/toluene, tetrahydrofuran/heptane and t-butylalcohol/hexane can also be used to achieve the desired solvent properties. The currently preferred solvent, because of the high yields of HPA which can be achieved under moderate reaction conditions, is methyl-t-butyl ether.

The catalyst is a non-phosphine-ligated cobalt carbonyl compound. Although phosphine-ligated catalysts are active for hydroformylation reactions, the invention process is designed to achieve good yield and selectivity without the additional expense of the ligand. The cobalt catalyst can be supplied to the hydroformylation reactor in essentially any form including metal, supported metal, Raney-cobalt, hydroxide, oxide, carbonate, sulfate, acetylacetonate, salt of a carboxylic acid, or as an aqueous cobalt salt solution, for example. It may be supplied directly as a cobalt carbonyl such as dicobaltoctacarbonyl or cobalt hydridocarbonyl. If not supplied in the latter forms, operating conditions can be adjusted such that cobalt carbonyls are formed in situ via reaction with $H_2$ and CO, as described in J. Falbe, "Carbon Monoxide in Organic Synthesis," Springer-Verlag, N.Y. (1970). In general, catalyst formation conditions will include a temperature of at least 50° C. and a carbon monoxide partial pressure of at least about 100 psig. For more rapid reaction, temperatures of about 120° to 200° C. should be employed, at CO pressures of at least 500 psig. Addition of high surface area activated carbons or zeolites, especially those containing or supporting platinum or palladium metal, can accelerate cobalt carbonyl formation from noncarbonyl precursors. The resulting catalyst is maintained under a stabilizing atmosphere of carbon monoxide, which also provides protection against exposure to oxygen. The most economical and preferred catalyst activation and reactivation (of recycled catalyst) method involves preforming the cobalt carbonyl under $H_2$/CO from cobalt hydroxide in the presence of a small amount of seed cobalt carbonyl. The conversion of $Co^{2+}$ to the desired cobalt carbonyl is carried out at a temperature within the range of about 75° to about 200° C., preferably about 100° to about 140° C. and a pressure within the range of about 1000 to about 5000 psig for a time preferably less than about 3 hours. The preforming step can be carried out in a pressurized preforming reactor or in situ in the hydroformylation reactor.

The amount of cobalt present in the reaction mixture will vary depending upon the other reaction conditions, but will generally fall within the range of about 0.01 to about 1 wt %, preferably about 0.05 to about 0.3 wt %, based on the weight of the reaction mixture.

The hydroformylation reaction mixture will preferably include a catalyst promoter to accelerate the reaction rate. Suitable promoters include sources of mono- and multivalent metal cations of weak bases such as alkali, alkaline earth and rare earth metal salts of carboxylic acids. Also suitable are lipophilic promoters such as lipophilic phosphonium salts and lipophilic amines, which accelerate the rate of hydroformylation without imparting hydrophilicity (water solubility) to the active catalyst. As used herein, "lipophilic" means that the promoter tends to remain in the organic phase after extraction of HPA with water. The promoter will generally be present in an amount within the range of about 0.01 to about 0.6 moles per mole of cobalt. Suitable metal salts include sodium, potassium and cesium acetates, propionates and octoates; calcium carbonate; and lanthanum acetate. The currently preferred metal salt, because of its availability and demonstrated promotion of ethylene oxide hydroformylation, is sodium acetate. The currently preferred lipophilic promoters are dimethyldodecyl amine and tetrabutylphosphonium acetate.

It is generally preferred to regulate the concentration of water in the hydroformylation reaction mixture, as excessive amounts of water reduce (HPA+PDO) selectivity below acceptable levels and may induce formation of a second liquid phase. At low concentrations, water can assist in promoting the formation of the desired cobalt carbonyl catalyst species. Acceptable water levels will depend upon the solvent used, with more polar solvents generally being more tolerant of higher water concentrations. For example, optimum water levels for hydroformylation in methyl-t-butyl ether solvent are believed to be within the range of about 1 to about 2.5 wt %.

Following the hydroformylation reaction, hydroformylation reaction product mixture 4 containing 3-hydroxypropanal, the reaction solvent, 1,3-propanediol, the cobalt catalyst and a minor amount of reaction by-products, is cooled and passed to extraction vessel 5, wherein an aqueous liquid, generally water and optional miscibilizing solvent, are added via 6 for extraction and concentration of the HPA for the subsequent hydrogenation step. Liquid extraction can be effected by any suitable means, such as mixer-settlers, packed or trayed extraction columns, or rotating disk contactors. Extraction can, if desired, be carried out in multiple stages. The water-containing hydroformylation reaction product mixture can optionally be passed to a settling tank (not shown) for resolution of the mixture into aqueous and organic phases. The amount of water added to the hydroformylation reaction product mixture will generally be such as to provide a water:mixture ratio within the range of about 1:1 to about 1:20, preferably about 1:5 to about 1:15. The addition of water at this stage of the reaction may have the additional advantage of suppressing formation of undesirable heavy ends. Extraction with a relatively small amount of water provides an aqueous phase which is greater than 20 wt % HPA, preferably greater than 35 wt % HPA, permitting economical hydrogenation of the HPA to PDO and recovery of PDO product. The water extraction is preferably carried out at a temperature within the range of about 25° to about 55° C., with higher temperatures avoided to minimize condensation products (heavy ends) and catalyst disproportionation to inactive, water-soluble cobalt species. In order to maximize catalyst recovery, it is optional but preferred to perform the water extraction under 50 to 200 psig carbon monoxide at 25° to 55°C.

The organic phase containing the reaction solvent and the major portion of the cobalt catalyst can be recycled from the extraction vessel to the hydroformylation reaction via 7. According to the invention, aqueous extract 8 is passed to second extraction vessel 9, wherein a fresh quantity of the non-water-miscible solvent such as methyl-t-butyl ether used for the hydroformylation reaction is added via 10 for extraction of cobalt carbonyl or cobalt-containing derivatives thereof remaining in the aqueous phase. It is desirable for process economics to recover and recycle to the hydroformylation step as much of this cobalt catalyst as possible. This second extraction step typically has been found to recover more than 30 wt %, and optimally recover more than 75 wt %, of the cobalt otherwise lost to the aqueous 3-hydroxypropanal phase following water extraction when used in combination with distillation or other means to concentrate cobalt in this recycle stream to the hydroformylation reaction. The process facilitates reaching the overall process objective of recovering and recycling at least about 99.6 wt % of the cobalt present in the hydroformylation reaction.

The solvent for this second extraction step can be any of those previously described for the hydroformylation reaction step; however, the preferred solvent will be the same as that chosen for the hydroformylation step, most preferably methyl-t-butyl ether. The solvent can be fresh "makeup" solvent or can be solvent recovered from downstream distillation.

This second-stage extraction is most efficiently carried out at a temperature within the range of about 25° to about 55° C. and a preferable but optional carbon monoxide pressure within the range of about 50 to about 200 psig. The process can be carried out by introducing the solvent into the aqueous phase with agitation, in the same or different vessel as for the water extraction step, and then allowing the organic and aqueous phases to resolve. In such a process, the solvent can be used in an amount within the range of about 3 to about 300 wt %, based on the amount of the liquid phase to be treated, depending on the process options available for recycling catalyst and solvent to the reaction. Alternatively, the cobalt-containing aqueous phase can be countercurrently contacted with the added solvent in a multi-staged vessel under the above conditions. The solvent phase from second-stage extraction containing recovered cobalt is recycled via 11, with optional concentration of cobalt by distillation or other means, to the hydroformylation reaction.

The decobalted aqueous product mixture 12 is passed to hydrogenation vessel 13 and reacted with hydrogen 14 in the presence of a hydrogenation catalyst to produce a hydrogenation product mixture 15 containing 1,3-propanediol. The hydrogenation step may also revert some heavy ends to PDO. The solvent and extractant water 17 can be recovered by distillation in column 16 and recycled to the water extraction process via a further distillation (not shown) for separation and purge of light ends. PDO-containing product stream 18 can be passed to distillation column 19 for recovery of PDO 20 from heavy ends 21.

Hydrogenation of the HPA to PDO can be carried out in aqueous solution at an elevated temperature during at least a portion of the hydrogenation step of about 40° C., generally within the range of about 50° to about 175° C., under a hydrogen pressure of at least about 100 psig, generally within the range of about 200 to about 2000 psig. The reaction is carried out in the presence of a fixed-bed hydrogenation catalyst such as any of those based upon Group VIII metals, including nickel, cobalt, ruthenium, platinum and palladium, as well as copper, zinc and chromium and mixtures and alloys thereof. The preferred catalysts are particulate nickel-based compositions. Hydrogenation is preferably carried out in three sequential temperature stages: a first stage at about 50 to about 70° C.; a second stage at about 70° to about 100° C.; and a third, high-temperature stage at greater than about 120° C. for reversion of heavy ends to 1,3-propanediol. Highest yields are achieved under slightly acidic reaction conditions.

EXAMPLE 1

This experiment was performed to determine if residual cobalt carbonyl hydroformylation catalyst could be removed from an aqueous solution of 3-hydroxypropanal obtained by water extraction of 3-hydroxypropanal from the reaction product mixture of cobalt carbonyl catalyzed ethylene oxide hydroformylation.

Two parts fresh methyl-t-butyl ether were added with agitation to one part of the aqueous 3-hydroxypropanal solution at room temperature under 600 psi 1:1 ($CO:H_2$) syngas. The phases were allowed to resolve. The "new" aqueous phase was removed, and both phases were analyzed by cobalt-specific colorimetry for cobalt. About 60% of the cobalt in the original water phase was removed.

EXAMPLE 2

A series of experiments was conducted in which aqueous intermediate product was sampled directly from one-gallon batch ethylene oxide hydroformylation reactions, following water extraction in the reactor at 25°–45° C. and 500–1300 psi 1:1 syngas. The aqueous product was transferred to a nitrogen-capped jar of nitrogen-sparged methyl-t-butyl ether. Off-gassing of syngas provided a syngas blanket over the jar. The jar was shaken to provide thorough contact of the aqueous phase with the MTBE, and the phases were allowed to separate. The cobalt content of each phase was assessed by colorimetry following acid digestion. Results are shown in Table 1. Cobalt recoveries by solvent re-extraction ranged from 5–80 percent, depending upon conditions employed.

TABLE 1

MTBE Re-Extraction of Aqueous Product For Cobalt Recovery

| Run | Co Initial UL (ppm) | Co Initial LL (ppm) | Ratio Re-extract MTBE/LL | Co Re-extract LL (ppm) | Co Re-extract MTBE (ppm) | % Recovery |
|-----|---------------------|---------------------|--------------------------|------------------------|--------------------------|------------|
| 1   | 2211                | 168                 | 0.34                     | 33                     | 400                      | 80         |
| 2   | 2266                | 132                 | 1.45                     | 52                     | 28                       | 44         |
| 3   | 2362                | 225                 | 3.33                     | 110                    | 52                       | 54         |
| 4   | 2325                | 208                 | 6.33                     | 142                    | 34                       | 39         |
| 5   | 2421                | 257                 | 3.06                     | 226                    | 54                       | 17         |
| 6   | 2581                | 187                 | 2.06                     | 185                    | 64                       | 5          |
| 7   | 2156                | 181                 | 0.17                     | 129                    | 407                      | 29         |
| 8   | 2102                | 92                  | 0.17                     | 64                     | 361                      | 31         |
| 9   | 2287                | 136                 | 0.10                     | 115                    | 238                      | 16         |
| 10  | 2156                | 130                 | 0.14                     | 62                     | 339                      | 57         |

% recovery = % of cobalt in original LL recoverable by re-extraction.
UL = Upper Layer
LL = Lower Level

EXAMPLE 3

Aqueous product from the first extraction stage of a continuous pilot plant PDO preparation process containing 25 wt % 3-hydroxypropanal intermediate and 67 ppm cobalt at a flow of 7.08 grams/minute was extracted with countercurrent fresh MTBE at 0.67 grams/min flow in a 30-inch tall by one-inch inside diameter extractor packed with plastic rings. Extraction was carried out at 40° C. under 1400 psi 3:1 $H_2$:CO. The cobalt level of the aqueous effluent from the second extractor was 43 ppm, giving 35% recovery of cobalt from the original feed. MTBE solvent exiting the top of the column contained 254 ppm cobalt. The flow rate of MTBE employed matched that required for makeup of MTBE lost from the hydroformylation system via the aqueous product. Higher extraction efficiencies would be expected from increased MTBE flow rates, with separation of catalyst and MTBE cycle a more concentrated cobalt/MTBE stream, as desired to maintain MTBE solvent inventory in the hydroformylation system.

We claim:

1. A process for preparing 1,3-propanediol comprising the steps of:

(a) contacting ethylene oxide with carbon monoxide and hydrogen in an essentially non-water-miscible solvent in the presence of an effective amount of a non-phosphine-ligated cobalt catalyst and an effective amount of a catalyst promoter under reaction conditions effective to produce an intermediate product mixture comprising less than 15 wt % 3-hydroxypropanal;

(b) adding an aqueous liquid to said intermediate product mixture and extracting into said aqueous liquid a major portion of the 3-hydroxypropanal so as to provide a first aqueous phase comprising 3-hydroxypropanal in greater concentration than the concentration of 3-hydroxypropanal in the intermediate product mixture, and a first organic phase comprising a major portion of the cobalt carbonyl or a cobalt-containing derivative thereof;

(c) separating the first aqueous phase from the first organic phase;

(d) adding fresh non-water-miscible solvent to the first aqueous phase and extracting into such solvent at least a portion of any cobalt catalyst or cobalt-containing derivative thereof present in such aqueous phase, to provide a second aqueous phase comprising 3-hydroxypropanal and a second organic phase comprising the cobalt catalyst or a cobalt-containing derivative thereof;

(e) separating the second aqueous phase from the second organic phase;

(f) passing the first organic phase and the second organic phase to the process of step (a);

(g) contacting the second aqueous phase comprising 3-hydroxypropanal with hydrogen in the presence of a hydrogenation catalyst under hydrogenation conditions to provide a hydrogenation product mixture comprising 1,3-propanediol; and (h) recovering 1,3-propanediol from said hydrogenation product mixture.

2. The process of claim 1 in which the non-water-miscible solvent of steps (a) and (d) comprises an ether.

3. The process of claim 1 in which the 3-hydroxypropanal in the intermediate product mixture is produced at a level within the range of about 5 to about 10 wt % based on said intermediate product mixture.

4. The process of claim 3 in which step (a) is carried out at a temperature within the range of about 50° to about 100° C.

5. The process of claim 4 in which step (a) is carried out at a pressure within the range of about 500 to about 5000 psig.

6. The process of claim 1 which further comprises carrying out steps (b) and (d) under carbon monoxide.

7. The process of claim 1 which further comprises carrying out step (d) by staged countercurrent contact between the fresh solvent and the first aqueous phase.

8. The process of claim 5 in which the non-water-miscible solvent of steps (a) and (d) is methyl-t-butyl ether.

9. The process of claim 1 in which the catalyst promoter comprises water present in step (a) in an amount within the range of about 1 to about 2.5 wt % water.

10. The process of claim 1 in which the solvent of step (d) is added in an amount within the range of about 3 to about 300 wt %, based on the weight of the aqueous phase.

11. The process of claim 1 in which step (d) is carried out at a temperature within the range of about 25° to about 55° C. and a carbon monoxide pressure within the range of about 50 to about 200 psig.

12. The process of claim 1 in which at least about 30 wt % of any cobalt carbonyl or cobalt-containing derivative thereof present in the first aqueous phase is removed in step (d).

13. The process of claim 11 in which the promoter is selected from lipophilic amines and lipophilic phosphonium salts present in an amount within the range of about 0.01 to about 0.6 moles per mole of cobalt.

14. The process of claim 1 in which the carbon monoxide and hydrogen of step (a) are present in an $H_2$/CO ratio within the range of about 1.5:1 to about 5:1.

15. The process of claim 1 in which step (a) is carried out at a temperature within the range of about 60° to about 90° C. and a pressure within the range of about 1000 to about 3500 psig.

16. The process of claim 1 in which at least about 99.6 wt % of cobalt present in step (a) is recovered and recycled to step (a).

17. The process of claim 1 in which step (b) is carried out at a temperature within the range of about 25° to about 55° C.

* * * * *